(12) United States Patent
Muller et al.

(10) Patent No.: US 9,468,411 B2
(45) Date of Patent: Oct. 18, 2016

(54) COMPACT MECHANISM FOR MOVING A COMPRESSION PADDLE

(75) Inventors: Serge Muller, Guyancourt (FR);
Aurelie Boudier, Bois d'Arcy (FR);
Regis Gerard Elle Personnelli, Buc (FR); Francois Lenfant, Le Chesnay (FR)

(73) Assignee: GENERAL ELECTRIC COMPANY, Shelton, CT (US)

(*) Notice: Subject to any disclaimer, the term of this patent is extended or adjusted under 35 U.S.C. 154(b) by 327 days.

(21) Appl. No.: 14/241,916

(22) PCT Filed: Aug. 28, 2012

(86) PCT No.: PCT/US2012/052694
§ 371 (c)(1),
(2), (4) Date: Sep. 18, 2014

(87) PCT Pub. No.: WO2013/033110
PCT Pub. Date: Mar. 7, 2013

(65) Prior Publication Data
US 2015/0023476 A1    Jan. 22, 2015

(30) Foreign Application Priority Data
Aug. 30, 2011  (FR) ...................... 11 57651

(51) Int. Cl.
*A61B 6/04* (2006.01)
*A61B 6/02* (2006.01)
*A61B 6/00* (2006.01)

(52) U.S. Cl.
CPC ............. *A61B 6/0457* (2013.01); *A61B 6/025* (2013.01); *A61B 6/0414* (2013.01); *A61B 6/502* (2013.01)

(58) Field of Classification Search
CPC .... A61B 6/025; A61B 6/032; A61B 6/4441; A61B 6/502; A61B 6/0414; A61B 6/0421; A61B 6/4405; A61B 6/44; A61B 6/4435; A61B 6/04; A61B 6/4447; G01N 23/046; G03B 42/04
USPC ............ 378/21, 37, 167, 177, 180, 189, 208
See application file for complete search history.

(56) References Cited

U.S. PATENT DOCUMENTS 5,018,176 A    5/1991  Romeas et al.
5,388,142 A    2/1995  Morris
(Continued)

FOREIGN PATENT DOCUMENTS

CN    201370591 Y    12/2009
CN    101879067 A    11/2010
(Continued)

OTHER PUBLICATIONS

Unofficial English Translation of French Search Report and Written Opinion issued from FR Application No. 1157647 on Nov. 22, 2011.
(Continued)

*Primary Examiner* — Jurie Yun
(74) *Attorney, Agent, or Firm* — GE Global Patent Operation; Marc A. Vivenzio

(57) ABSTRACT

A mammography or tomosynthesis apparatus, comprising a mechanism configured to move a paddle, relative to a detector platform fixed to a main body of the apparatus, to compress a patient's breast against the detector platform to form a surface. The mechanism comprises a post that is mobile relative to the detector platform and/or to the body and configured so that maximum extension of the post relative to the surface follows the movements of the paddle relative to the detector platform.

10 Claims, 7 Drawing Sheets

(56) References Cited

U.S. PATENT DOCUMENTS

| | | |
|---|---|---|
| 2005/0111617 A1 | 5/2005 | Shoji |
| 2005/0276379 A1 | 12/2005 | Polichar et al. |
| 2007/0133738 A1 | 6/2007 | Zimmermann |
| 2007/0206723 A1 | 9/2007 | Okada et al. |
| 2008/0080668 A1 | 4/2008 | Kashiwagi |
| 2010/0191105 A1 | 7/2010 | Bowers et al. |
| 2012/0163537 A1* | 6/2012 | Iwakiri ................ A61B 6/4283 378/62 |

FOREIGN PATENT DOCUMENTS

| | | |
|---|---|---|
| EP | 0390653 | 10/1990 |
| FR | 2882246 | 8/2006 |
| JP | 2007289225 A | 11/2007 |
| WO | 2008109247 A1 | 9/2008 |

OTHER PUBLICATIONS

PCT Search Report and Written Opinion issued in connection with corresponding PCT Application No. PCT/US2012/052676 on Sep. 28, 2012.

Unofficial English Translation of Chinese Office Action and Search Report issued from CN Application No. 201280041129.6 on May 6, 2015.

Unofficial English Translation of Chinese Office Action ind Search Report issued from CN Application No. 201280042671.3 on Jun. 9, 2015.

Translation of FR Written opinion from corresponding French Application No. 1157651, dated Nov. 29, 2011.

FR Search Report from corresponding French Application No. 1157651, dated Nov. 29, 2011.

PCT Search Report and Written Opinion from corresponding PCT Application No. PCT/US12/052694, dated Oct. 16, 2012.

\* cited by examiner

Prior Art

COMPACT MECHANISM FOR MOVING A COMPRESSION PADDLE

TECHNICAL FIELD

The present invention concerns apparatus for mammography or tomosynthesis.

BACKGROUND

As shown in FIG. 1, equipment 1 is a known mammography apparatus.

Said mammography equipment allows for two-dimensional medical images to be obtained, in particular using X-ray radiography.

For this purpose, said known equipment 1 conventionally comprises: at least one X-ray source 2 comprising an X-ray emitting tube 21, and a detector platform 3 arranged opposite the source 2 and intended to receive and give support to a patient's breast (not illustrated).

The detector platform 3 conventionally comprises a breast support tray 30 that is substantially transparent or has little X-ray attenuation, and integrates a detector 31 for detecting the X-rays after they have passed through the patient's breast.

The detector 31 may conventionally be an array of sensors or an X-ray sensitive film cassette, or any other X-ray detector known to persons skilled in the art.

The detector platform 3 and the X-ray source 2 are carried by a common gantry 5 possibly having an angular range a around a central axis A-A', relative to the detector platform 3 and the source 2, for scanning different viewing angles desired for mammography.

To take into account different patient heights, the gantry 5 is slidably mounted in a vertical structure 6. The gantry 5 can therefore be raised or lowered by a distance δ within the vertical structure 6.

Additionally, the apparatus 1 conventionally comprises a compression plate 4, known as a paddle by those skilled in the art, used to compress the breast against the detector platform 3 when taking images.

The paddle 4 is connected to a carriage 7 mounted in translation on the gantry 5 along a rail 8 extending immobile over the gantry 5 relative to the detector platform 3.

The movement of the carriage 7 along the rail 8 can be motorized or performed manually by means of thumbwheels 71, for example.

The apparatus in FIG. 1 has disadvantages however.

The rail 8 extends immobile over the gantry 5 relative to the detector platform 3, and in addition lies entirely above the detector platform 3.

The rail 8, therefore, permanently takes up space in this upper part of the detector platform 3.

In addition, when the gantry 5 is moved over its angular range α, at some points it may cause pinching of the patient's breast during mammography or tomosynthesis, i.e., an entire sequence of radiographic images in a single cycle, allowing a three-dimensional radiological image of the patient's breast to be obtained. Equipment is, therefore, known, which comprises a source positioned on a support dissociated from the detector platform.

On account of the large amount of upper space that is taken up permanently, it is also difficult to access the patient's breast above the detector platform 3 when positioning the breast or during a procedure such as biopsy of the breast, for example, guided by the mammography or tomosynthesis image.

SUMMARY OF THE INVENTION

Embodiments of the present invention overcome at least one of these disadvantages.

For this purpose, mammography or tomosynthesis apparatus is provided according to an embodiment of the present invention, comprising: a mechanism for moving a paddle relative to a detector platform fixed to a main body of the apparatus, to compress a patient's breast against the detector platform forming a surface, characterized in that the mechanism comprises a post mobile relative to the detector platform and/or the body, and adapted so that maximum extension of the post relative to the surface follows the movements of the paddle relative to the detector platform.

Embodiments of the present invention are completed by the following characteristics taken alone or in any possible technical combination thereof: the post is mounted slidably in at least one corresponding receiver of the main body of the apparatus and/or the detector platform; the post forms a block supporting a carriage connected to the paddle; the post forms a block supporting a carriage connected to an arm connected to the paddle; the post comprises at least two rods mounted slidably in at least two corresponding tubes provided in the main body of the apparatus and/or the detector platform; the post is telescopic relative to the main body of the apparatus and/or the detector platform; the post forms a block supporting a carriage connected to the paddle; the post comprises at least two rods supporting a carriage connected to the paddle; the post is scissor-hinged; and the apparatus is of ultra-portable type and/or of C-arm type dissociated from the detector platform.

Embodiments of the present invention have numerous advantages.

By means of the post, mobile relative to the body of the apparatus and/or the detector platform, and adapted so that maximum extension of the post relative to the surface of the detector platform follows the movements of the paddle relative to the detector platform and/or the body, the mechanism takes up less space above the detector platform. In particular when the paddle is in the bottom position, which allows incorporation of the mechanism in: mammography apparatus known to persons skilled in the art, when it is desired to increase the compactness of the equipment, apparatus comprising a source positioned on a support dissociated from the detector platform and/or ultra-portable apparatus.

Users of apparatus incorporating embodiments of the present invention have more room for positioning the breast on the detector platform, and it is also easier to access the patient's breast above the detector platform when positioning the breast or for procedures, such as biopsy of the breast, guided by the mammography or tomosynthesis image.

BRIEF DESCRIPTION OF THE DRAWINGS

Other characteristics and advantages of the invention will become apparent from the following description which is solely illustrative and non-limiting, and is to be read with reference to the appended drawings in which.

In all figures, similar parts carry identical reference numbers.

DETAILED DESCRIPTION

As can be ascertained in FIGS. 2 to 7, an embodiment of the present invention concern mammography or tomosynthesis apparatus 1, comprising a mechanism for moving a paddle 4 relative to a detector platform 3 fixed to a main body 6 of the apparatus 1, to compress a patient's breast against a detector platform 3 forming a surface S.

Figure 1:
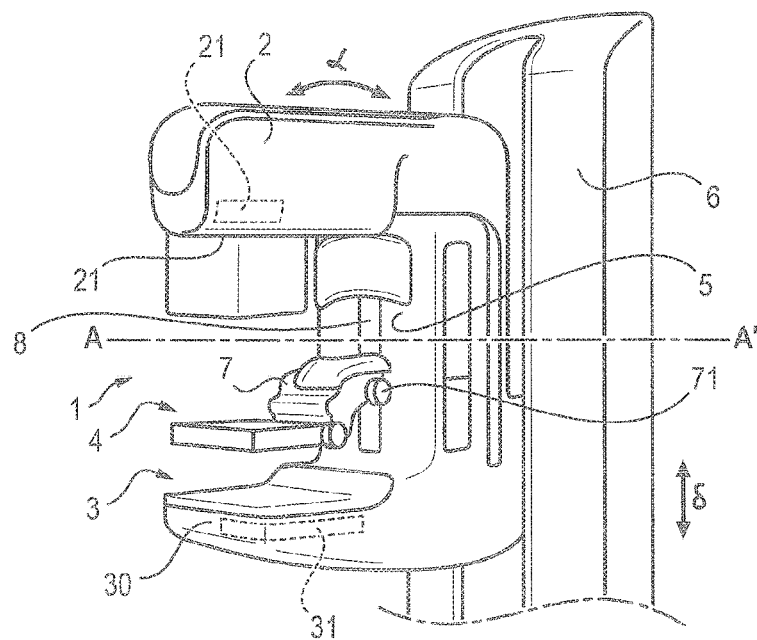
FIG. 1 shows mammography apparatus known in the prior art.

The apparatus 1 comprises all the conventional constituent parts presented in the introductory part of the present description with reference to FIG. 1; these parts of the description will not be reproduced for reasons of clarity and conciseness.

Within the main body 6 all electric and electronic means are comprised, which are known per se and required for controlling the generation of X-rays and at least for acquiring and even for processing the images derived from the X-ray detector 31.

The powering of all the electric and electronic means of the body 6 is, in an embodiment, obtained from the mains or optionally by battery.

In all the embodiments described in more detail in the present description, the displacing mechanism comprises a post, mobile relative to the body 6 and/or the detector platform 3, and adapted so that maximum extension thereof identified by h or h' in FIGS. 2 to 7, relative to the surface S, follows the movement of the paddle 4 relative to the detector platform 3. The surface S may be planar or curved.

First General Embodiment

According to a first general embodiment, the mechanism comprises a post, which is slidably mounted in at least one corresponding receiver provided in the main body 6 of the apparatus 1 and/or the detector platform 3.

Figure 2:
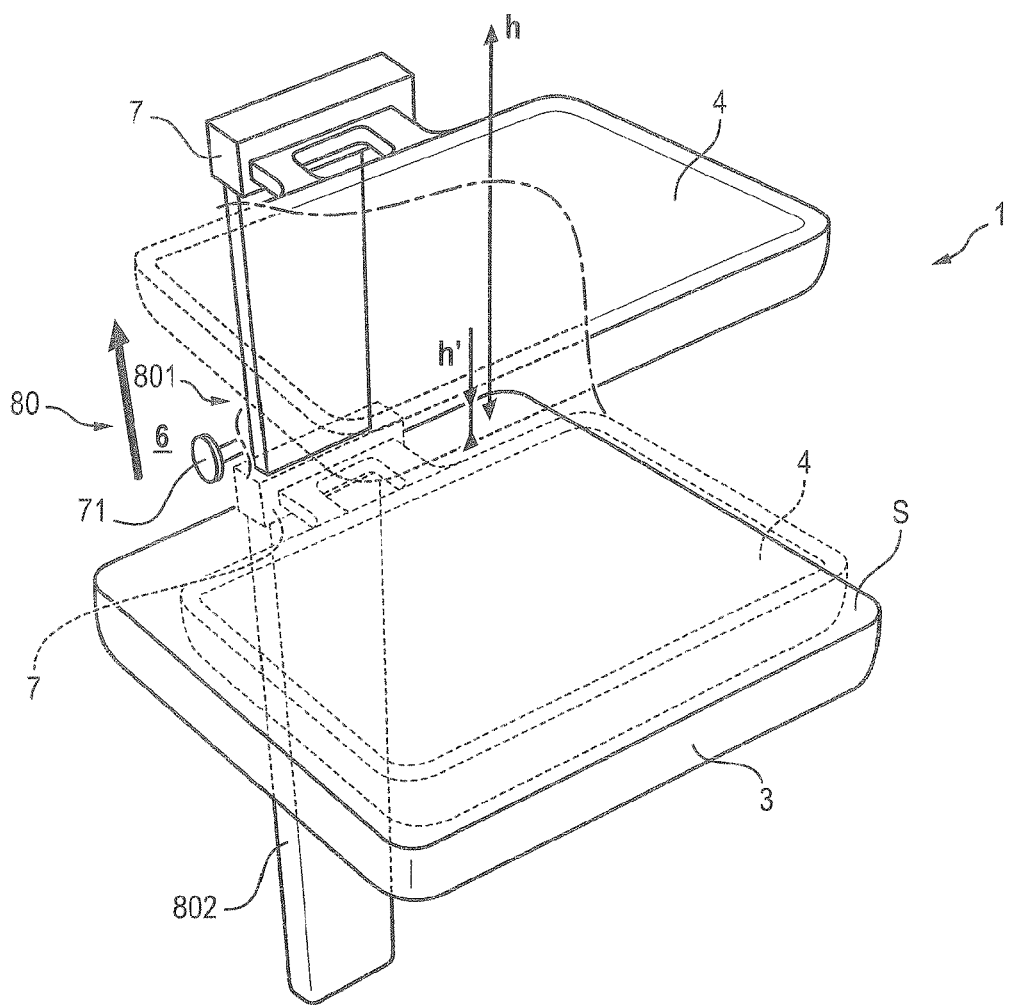
FIG. 2 illustrates one possible embodiment of a mechanism comprising a sliding block.

One first embodiment of a mechanism 80 comprising a said post 801 is schematically illustrated in FIG. 2.

The post 801 forms a rigid block supporting the carriage 7 connected to the paddle 4. It will be understood that a receiver 802 in which the post 801 is slidably mounted, has a corresponding inner profile.

The post-forming block 801 is a solid block, and has an oblong shape whose length is substantially equal to the travel distance needed for the carriage 7 and paddle 4.

The travel of the post block 801 within the receiver 802 is continuous, but chiefly has two positions: a top position h for placing the breast on the detector platform 3 and a bottom position h' for compressing the breast on the detector platform 3. In both cases, it is noted that the maximum extension of the post 801 identified by h or h' in FIG. 2, relative to the surface S, follows the movement of the paddle 4 relative to the detector platform 3.

The carriage 7, connected to the paddle 4, is located in an upper position on the free end of the post 801.

On the other hand, the receiver 802 is located in a lower position relative to the surface S of the detector platform 3, which means that the mechanism 80 for moving the paddle 4 extends on either side of the surface S of the detector platform 3. It will, therefore, be understood that the mechanism 80 for moving the paddle 4 takes up less space over the upper part of the detector platform 3 compared with the prior art in FIG. 1, thereby allowing the incorporation of the mechanism 80 in an ultra-portable apparatus, for example.

Figure 3:
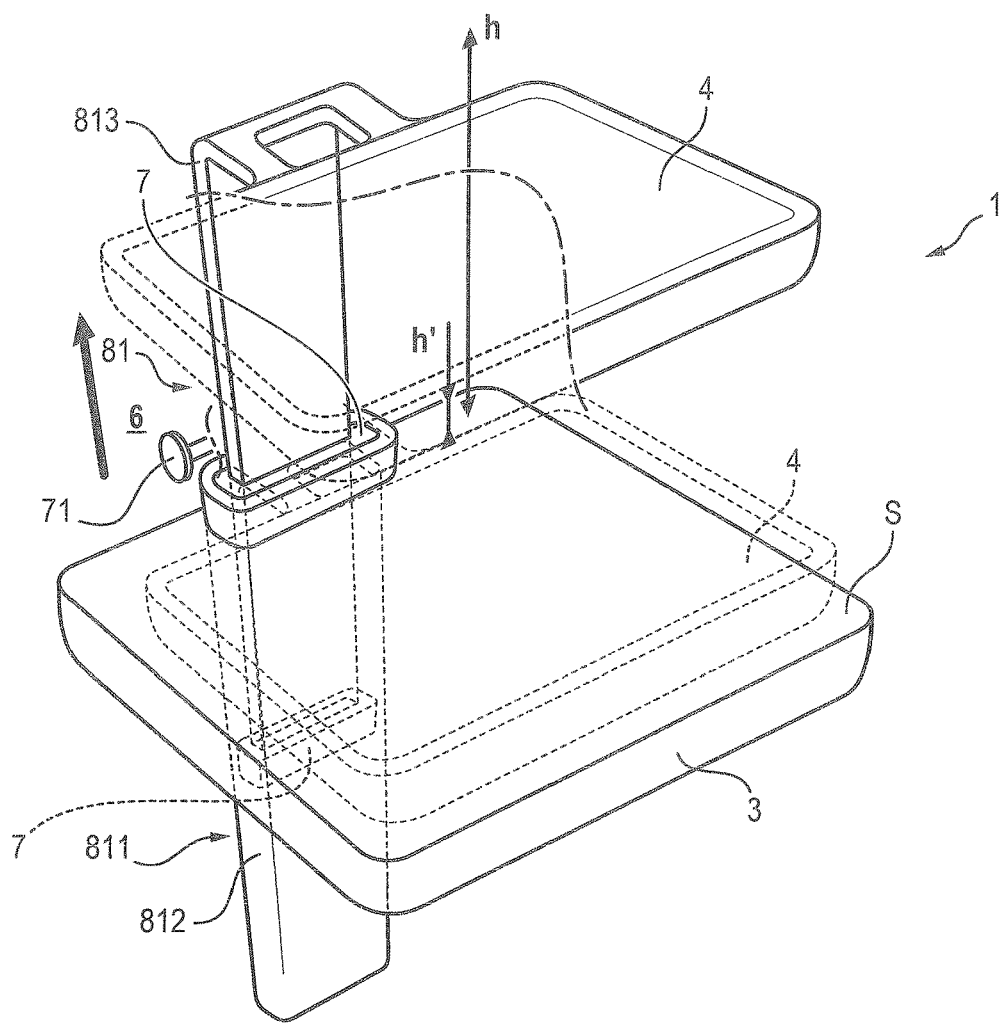
FIG. 3 illustrates one possible embodiment of a mechanism comprising a sliding block connected to a supporting arm of the paddle.

A second possible embodiment of a mechanism 81 comprising a post 811 mounted slidably in a corresponding receiver 812 provided in the main body 6 of the apparatus 1 and/or the detector platform 3 is illustrated in FIG. 3.

The post 811 forms a block supporting the carriage 7 connected to an arm 813, itself connected to the paddle 4.

Therefore, instead of being positioned in the upper position on the free end of the post 811, as is the case for the embodiment in FIG. 2, the carriage 7 lies at an intermediate position relative to the mechanism 81 for moving the paddle 4.

The arm 813, therefore, extends parallel to the post 811 and is connected to the paddle 4 by means of an elbow 8131.

As previously described, the post 811, therefore, moves inside the receiver 812 placed in a lower position relative to the surface 3 of the detector platform 3, so as to cause the paddle 4 to move upwards or downwards, by way of the arm 813, relative to the detector platform 3.

The arm 813 is, therefore, able to have two end positions: a top position h and a bottom position h' relative to the detector platform 3.

It will, therefore, be understood that the end-to-end extension of the post 811 follows the movement of the paddle 4 relative to the detector platform 3.

The cross-section of the block of posts 801 and 811 is rectangular, but other shapes can evidently be provided.

Figure 4:
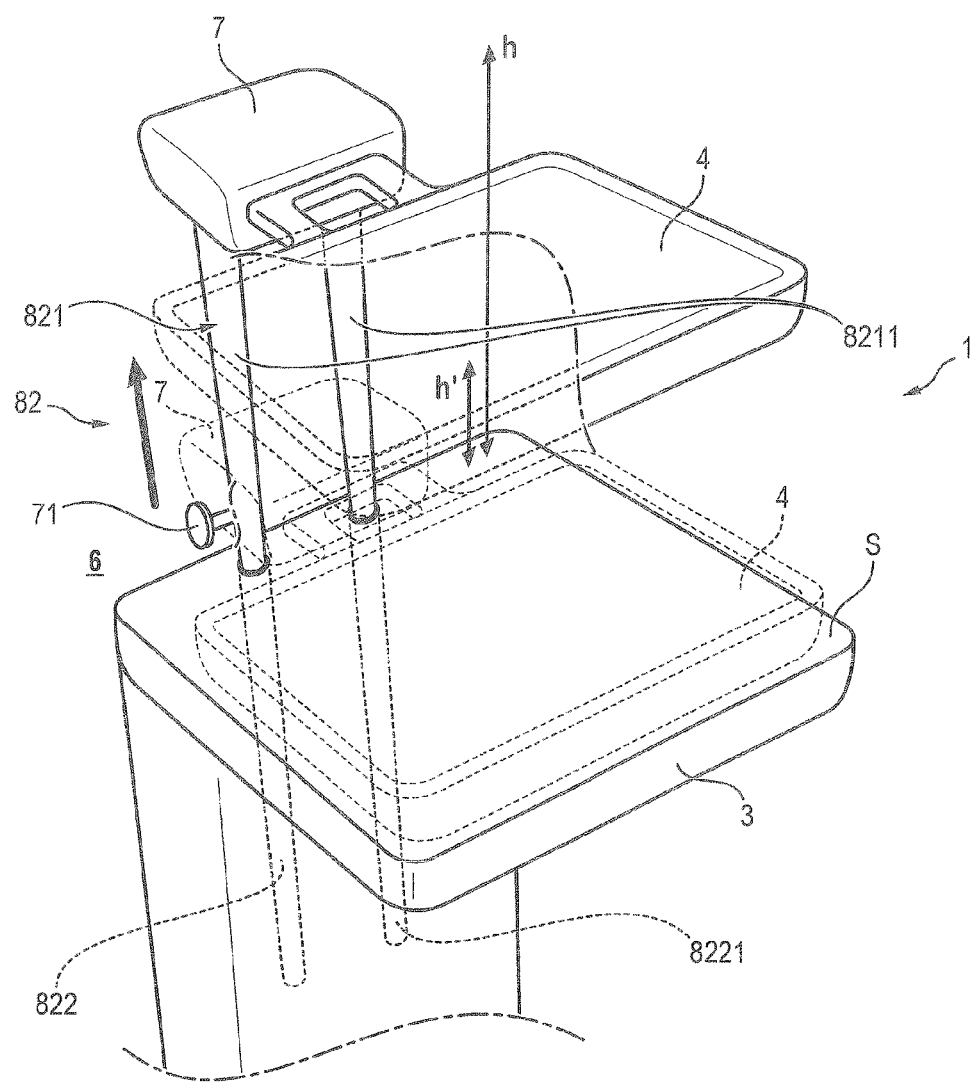
FIG. 4 shows one possible embodiment of a mechanism comprising two sliding rods.

FIG. 4 schematically illustrates a third possible embodiment of a mechanism 82 comprising a post 821 mounted slidably in at least one corresponding receiver 822 in the main body 6 of the apparatus 1 and/or the detector platform 3.

As can be ascertained in FIG. 4, the post 821 comprises at least two rigid rods 8211 mounted slidably in at least two tubes 8221 of mating inner shape and provided in the main body 6 of the apparatus 1 and/or in the detector platform 3.

The carriage 7 is, in an embodiment, placed in upper position on the free end of the rods 8211.

As previously described, the mechanism 82 extends on both sides of the surface S of the detector platform 3, and the carriage 7 has two end positions relative to the detector platform 3, namely, a top position h and a bottom position h'.

The cross-section of the rods 8211 is circular, for example, but other shapes of cross-section can evidently be provided.

The raising and lowering of the post 801, 811 or 821 in the receiver 802, 812 or 822, respectively, can be obtained in any manner known to persons skilled in the art, e.g., by mechanical cooperation of a rack with a cogged wheel, a worm screw, or a pneumatic or hydraulic cylinder, etc.

The movement of the post 801, 811 or 821 within the receiver 802, 812 or 822 may be manual by means of a thumb-wheel 71, for example, and/or it can be motorized.

Second General Embodiment

According to a second general embodiment, the mechanism comprises a post, which is telescopic relative to the main body 6 of the apparatus 1 and/or the detector platform 3.

Figure 5:
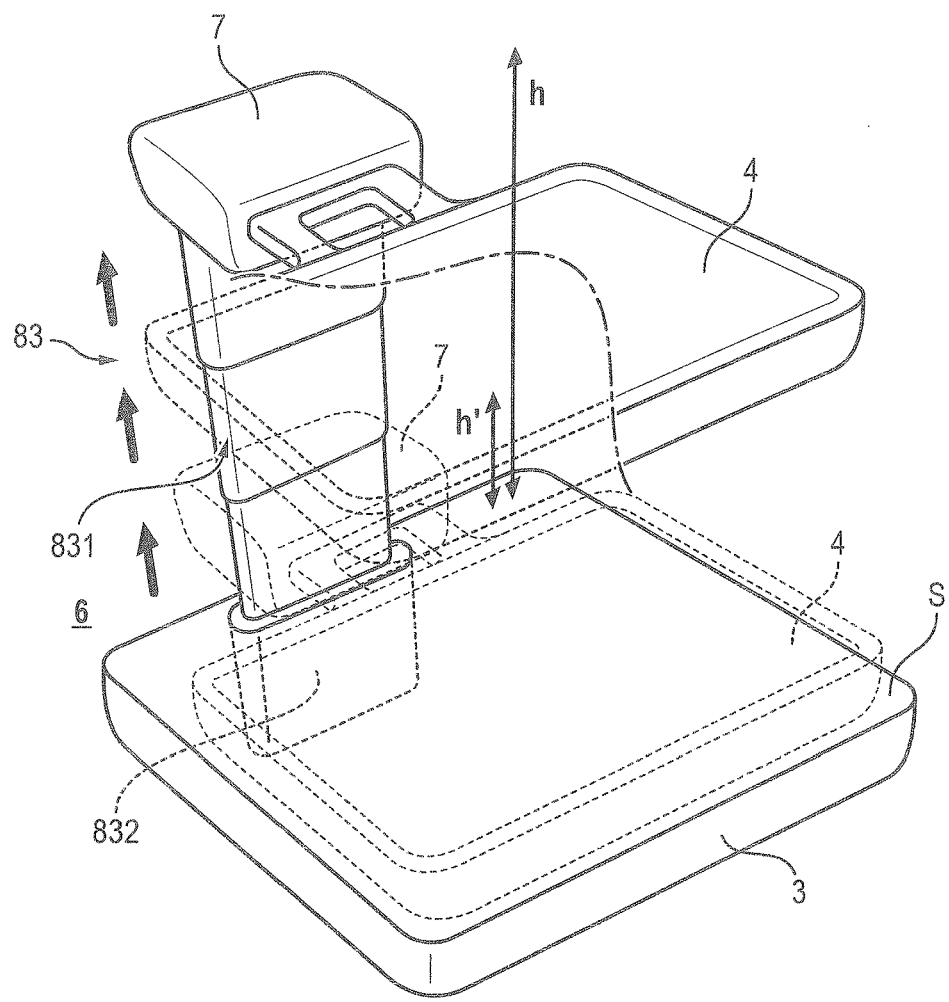
FIG. 5 shows one possible embodiment of a mechanism comprising a telescopic block.

A first possible embodiment of a mechanism 83 comprising said post 831 is illustrated in FIG. 5.

The post 831 forms a telescopic block supporting the carriage 7 connected to the paddle 4, at the upper part on the free end of the block.

The block 831 may comprise three tiers, for example, but a different number may also be provided.

Figure 6:
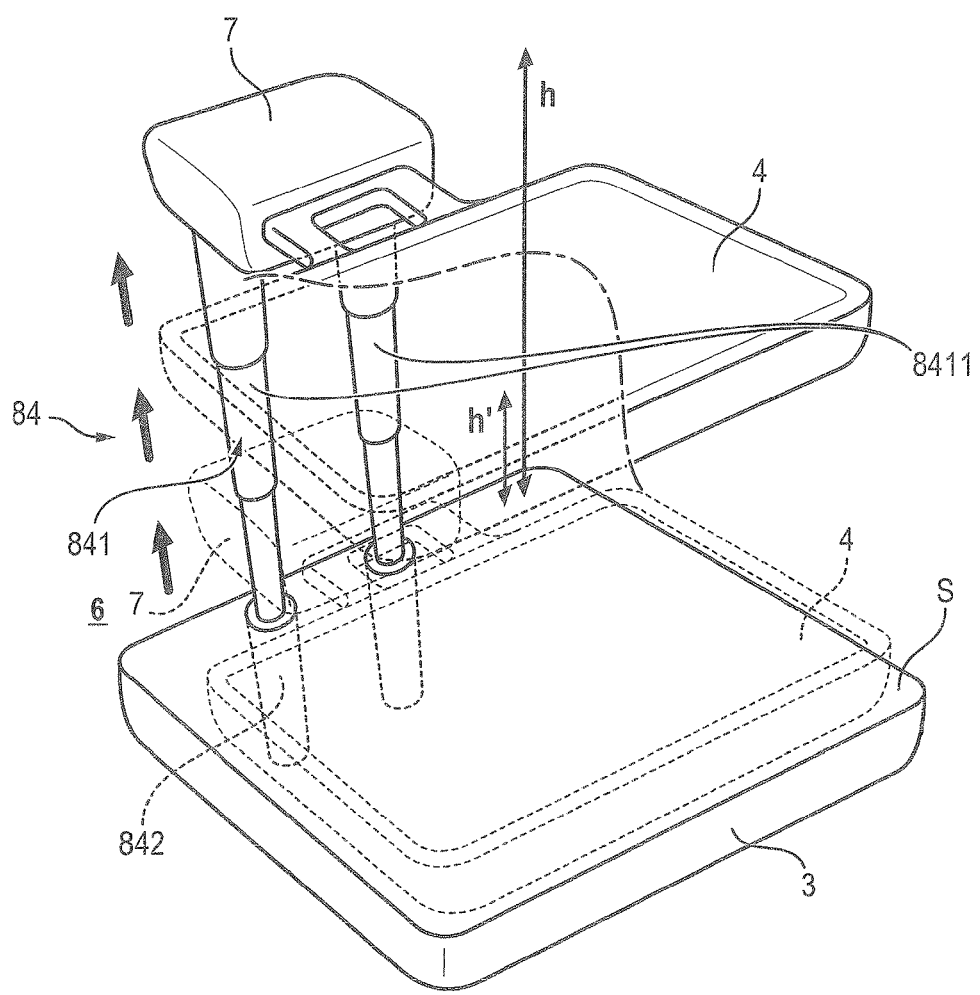
FIG. 6 shows one possible embodiment of a mechanism comprising two telescopic rods.

According to a second possible embodiment of a mechanism 84 comprising a said post 841 illustrated in FIG. 6, the post 841 comprises at least two telescopic rods 8411 supporting the carriage 7 connected to the paddle 4, at the upper part on the free end of the rods 8411.

In both cases, the telescopic post 831 or 841 is mobile relative to the detector platform 3 and/or the body 6 between an end top position denoted h and a bottom end position h' for the carriage 7.

As can be ascertained in FIGS. 5 and 6, the block 831 or the rods 8411 can be received in retracted position, but not limited thereto, in a receiver 832 or 842 of mating shape provided in the main body 6 of the apparatus 1 and/or in the detector platform 3. Therefore, the mechanism 83 or 84 extends on either side of the surface S of the detector platform 3.

The cross-section of the telescopic block 831 is rectangular, for example, and the cross-section of the rods 8411 is circular, for example, but other shapes of cross-section can evidently be provided.

The raising and lowering of the post 831 or 841 inside the receiver 832 or 842 in particular, but is not limited thereto, may be obtained by any manner known to those skilled in the art, e.g., by mechanical cooperation of hollow or telescopic worm screws, or a hydraulic or pneumatic cylinder, etc.

The movement of the post 831 or 841 may be manual by means of a thumb-wheel 71, for example, or it may be motorized.

Third General Embodiment

According to a third general embodiment, the apparatus 1 comprises a mechanism comprising a post 851 which is scissor-hinged.

Figure 7:
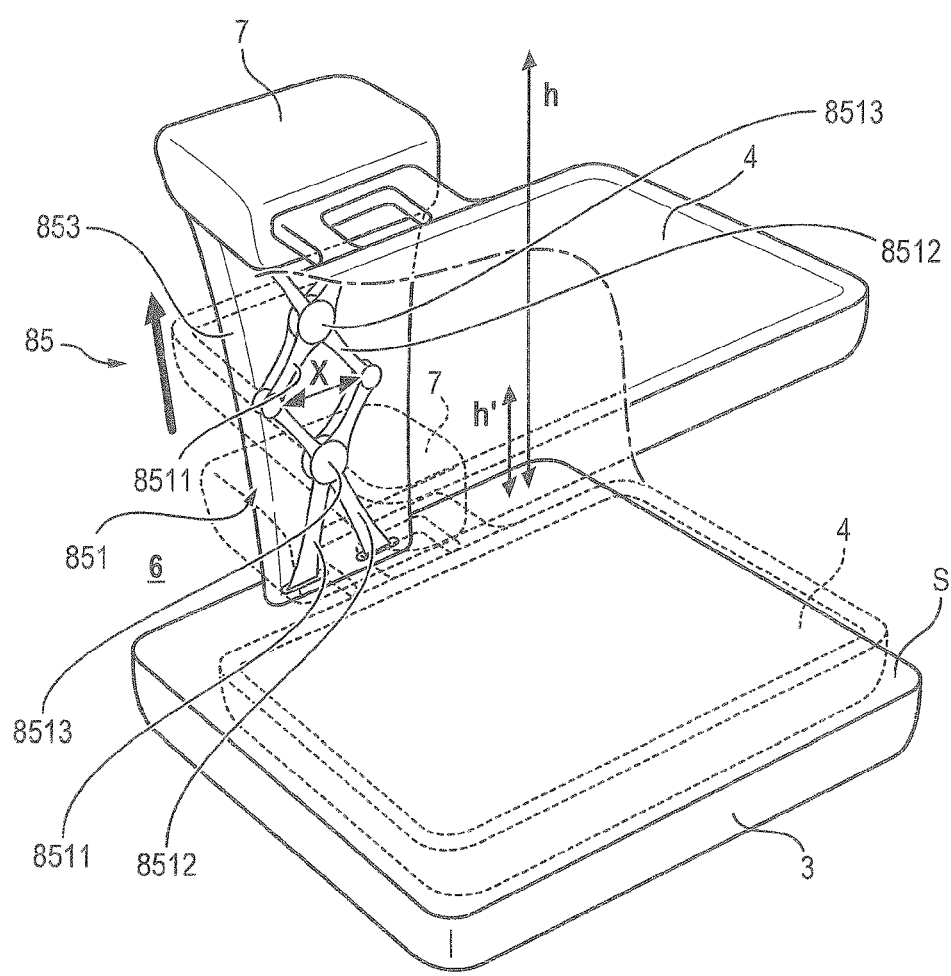
FIG. 7 shows one possible embodiment of a mechanism comprising scissor-hinged arms.

As shown in FIG. 7, the post 851 comprises at least one tier, each tier comprising at least two arms 8511 and 8512 crossed in an X-shape and hinged substantially at their center by means of a pivot link 8513, to form a scissor-like structure, therefore, capable of moving the carriage 7, connected to the paddle 4, upwards or downwards in relation to the x-spacing of the arms 8511 and 8512.

In FIG. 7, the post 851 comprises two tiers, but any number of tiers may evidently be provided.

The mechanism 85 also comprises a protection 853 around the post 851 to prevent problems related to possible pinching of a user or patient in the hinged post 851.

Said protection 853 can be formed of an elastic fabric, for example, or of a rigid telescopic structure, for example.

As previously described, the movement of the post 851 may be manual or motorized.

A carriage 7 has been described placed in an intermediate position of the mechanism with reference to FIG. 3, the carriage 7 being connected to an arm 813 itself connected to the paddle 4; it will evidently be understood that said carriage 7 and said arm 813 may be applied as a variant to the embodiments described in the other figures.

The embodiments in FIGS. 2 to 7 apply, but in non-limiting manner, to a apparatus which is "ultra-portable," i.e., whose weight is less than 100 kg. In some embodiments, the apparatus weighs less than 80 kg or between 60 kg and 40 kg.

Said apparatus comprises a retracted position for storage and/or transport and a deployed position for normal operation.

Providing a post according to the embodiments in FIGS. 2 to 7 increases the compactness of the main body of the apparatus.

The embodiments in FIGS. 2 to 7, also apply to mammography or tomosynthesis apparatuses comprising an X-ray source positioned on a support dissociated from the detector platform.

This written description uses examples to disclose the various embodiments, including the best mode, and also to enable any person skilled in the art to practice the embodiments, including making and using any devices or systems and performing any incorporated methods. The patentable scope of the embodiments is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A mammography or tomosynthesis apparatus comprising:
    a paddle moving mechanism configured to move a paddle, relative to a detector platform fixed to a main body of the apparatus, to compress a patient's breast against the detector platform to form a surface,
    wherein the paddle moving mechanism comprises:
        a post, mobile relative to the detector platform and/or to the body, configured so that movement of the post relative to the surface follows the movements of the paddle relative to the detector platform.

2. The apparatus according to claim 1, wherein the post is slidably mounted in at least one corresponding receiver in the main body of the apparatus and/or the detector platform.

3. The apparatus according to claim 2, wherein the post forms a block configured to support a carriage connected to the paddle.

4. The apparatus according to claim 2, wherein the post forms a block configured to support a carriage connected to an arm connected to the paddle.

5. The apparatus according to claim 2, wherein the post comprises at least two rods slidably mounted in at least two corresponding tubes in the main body of the apparatus and/or the detector platform.

6. The apparatus according to claim 1, wherein the post is telescopic relative to the main body of the apparatus and/or the detector platform.

7. The apparatus according to claim 6, wherein the post forms a block configured to support a carriage connected to the paddle.

8. The apparatus according to claim 6, wherein the post comprises at least two rods configured to support a carriage connected to the paddle.

9. The apparatus according to claim 1, wherein the post is scissor-hinged.

10. The apparatus according to claim 1, wherein the apparatus is of an ultra-portable type and/or a C-arm type dissociated from the detector platform.

* * * * *